United States Patent [19]
Miller et al.

[11] Patent Number: 6,025,360
[45] Date of Patent: *Feb. 15, 2000

[54] USE OF THEOPHYLLINE FOR THE MANUFACTURE OF A MEDICAMENT FOR THE TREATMENT OF ASTHMA

[75] Inventors: Allan John Miller, Thames Ditton; Christopher John McDonald; Michael Court, both of Cambridge, all of United Kingdom

[73] Assignee: Euro-Celtique, S.A., Luxembourg, Luxembourg

[ * ] Notice: This patent issued on a continued prosecution application filed under 37 CFR 1.53(d), and is subject to the twenty year patent term provisions of 35 U.S.C. 154(a)(2).

[21] Appl. No.: 08/652,495

[22] PCT Filed: Dec. 5, 1994

[86] PCT No.: PCT/GB94/02657

§ 371 Date: Sep. 6, 1996

§ 102(e) Date: Sep. 6, 1996

[87] PCT Pub. No.: WO95/15164

PCT Pub. Date: Jun. 8, 1995

[30] Foreign Application Priority Data

Dec. 3, 1993 [GB] United Kingdom .................. 9324860

[51] Int. Cl.$^7$ .................................................. A61K 31/52
[52] U.S. Cl. ............................................................ 514/263
[58] Field of Search ............................................ 514/263

[56] References Cited

U.S. PATENT DOCUMENTS 5,068,233 11/1991 Achterrath-Tuckerman et al. . 514/212

FOREIGN PATENT DOCUMENTS

| | | |
|---|---|---|
| 0134290 | 3/1985 | European Pat. Off. . |
| 0235363 | 9/1987 | European Pat. Off. . |
| 0407651 | 1/1991 | European Pat. Off. . |
| 2163957 | 3/1986 | United Kingdom . |
| 2164556 | 3/1986 | United Kingdom . |

OTHER PUBLICATIONS

USP Drug Information, tenth edition, vol. 1A, 706–707, 1990.
Magnussen et al., Am. Rev. Resp. Dis., 136(5), 1987, pp. 1163–1167.
Van Bever et al., Drugs, 44/1 (1992) pp. 36–46, abstract.
Remington's Pharmaceutical Sciences (1990) 18$^{th}$ ed. Mack Publishing. pp. 867–7.
"Immune Modulation By Theophylline: The Effect of Withdrawal of Chronic Treatment in Asthma," JC Kidney et al., Am Rev Rspir Dis 1993; 147 (4 pt 2): A772.
"Theophylline—an Immunomodulatory Role in Asthma?," Anne J. M. Ward et al., Am Rev Respir Dis vol. 147. pp. 518–523, 1993.
Ralph E. Howell, "Multiple Mechanisms of Xanthine Actions on Airway Reactivity, The Journal of Pharmacology and Experimental Therapeutics", vol. 255, No. 3, pp. 1008–1014, 1990.
J.P. Tarayre, et al., "Pharmacological Modulation of a Model of Bronchial Inflammation after Aerosol–Induced Active Anaphylactic Shock in Conscious Guinea Pigs", Int. J. Immnunopharmac., vol. 13, No. 4, pp. 349–356, 1991.
M. Bachelet, et al., "Interactions Between Cyclic AMP Stimulating Drugs and PAF–acether in Guinea Pig Alveolar Macrophages", Agents and Actions, vol. 26, 1/2, 1989.
M. Matejcek, et al., "Determination of the Central Effects of the Asthma Prophylactic Ketotifen, the Bronchodilator Theophylline, and both in Combination: An Application of Quantitive Electrocenphalography to the Study of Drug Interactions", Int. Journ. of Clin. Pharmac., Therapy and Toxicology, vol. 23, No. 5, pp. 258–266, 1985.
B. Bose, et al., "A Once Daily Theophylline Preparation in Prevention of Nocturnal Symptoms in Childhood Asthma", Eur. J. Pediatrics, 146: 524–527, 1987.
P.J. Barnes, et al., "Theophylline in the Management of Asthma Time for Reappraisal?", Eur. Respir. Jour., 7, 579–591, 1994.
Paul A. Mitenko, M.D., et al., "Rational Intravenous Doses of Theophylline", New Eng. J. Med. 289:600–603, 1973.
T.H. Self, Ph.D. et al., Reassessing the Therapeutic Range for Theophylline on Laboratory Report Forms: The Importance of 5–15 $\mu$g/ml, Pharmacotherapy, vol. 13, No. 6, 1993.
T. Fitzsimons, M.D. et al., "Mild Asthma", Allergy Proc., pp. 165–166, vol. 11, No. 4, Jul.–Aug. 1990.
Carl G.A. Persson, Ph.D., Overview of Theophylline, J. Allergy Clin. Immunol., Oct. 1986.
A. Tenabene et al., "The Treatment of Asthma by Theophylline", La Tunisie Medicale, vol. 71, No.6/7, p. 295, Jun./Jul. 1993.
M. Weinberger, M.d., "The Pharmacology and Therapeutic Use of Theophylline", The Journ. of Allergy and Clin. Immun., vol. 73, No. 5, I, May 1984.
T.J. Torphy, "Phosphodiesterase Inhibitors: New Opportunities for the Treatment of Asthma", Thorax, vol. 46, 1991.
I. Roitt et al., Immunology, p. 22, Mosby Inc., Phila.,1996.
F.S. Rosen et al., Case Studies in Immunology, p. 73–79, Current Biology Ltd., Philadelphia, P.A. 1997.

*Primary Examiner*—Phyllis G. Spivack
*Attorney, Agent, or Firm*—Davidson, Davidson & Kappel, LLC

[57] ABSTRACT

A prophylactic treatment for the inflammatory condition associated with chronic asthma is disclosed comprising administering theophyline or pharmaceutically acceptable salts thereof to provide a mean steady state plasma level of 1 to less than 5 mg/L.

6 Claims, No Drawings

USE OF THEOPHYLLINE FOR THE MANUFACTURE OF A MEDICAMENT FOR THE TREATMENT OF ASTHMA

This invention is concerned with pharmaceutical usages and compositions, particularly for the prophylaxis or treatment of asthma.

Asthma is a widespread disease, the particular mechanisms and aetiology of which have been and still are the subject of investigation and debate. Nevertheless it is generally accepted that asthma arises as the result of a specific or non-specific immune reaction within the lungs. The early bronchoconstrictive phase (Early Asthamitic Reaction, EAR) may be attributed to the release of histamine from mast cells in the lung tissue. Following this early phase the late asthmatic reaction (LAR) is characterized by infiltration of the lung with inflammatory cells comprising of eosinophils, lymphocytes, macrophages and neutrophils. In particular the eosinophil is known to directly damage lung tissue by release of cationic proteins. Attendant to this inflammatory infiltrate, are sub-epithelial changes in the bronchial airways which chronically lead to fibrosis and a reduction in the compliance of the pulmonary tissue. Orchestration of this cellular inflammation rests with the T lymphocytes which responds to specific and non-specific antigens inhaled into the lung. These antigens are absorbed on to the surface of cells such as macrophages before presentation to the T lymphocytes.

A variety of medicaments are, and have been, used in the treatment of the asthmatic condition. These can broadly be divided into those that effect a bronchodilatory change in the bronchoconstricted airways and those which effect a change in the underlying bronchial airway inflammation. An example of the first category are compounds such as salbutamol, an inhaled $\beta_2$ agonist and an example of the latter category is "inhaled steroid" such as Beclomethasone or Budesonide.

The present invention is predicated on the unexpected finding that theophylline, a known bronchodilatory used in the treatment of asthma has an immunomodulating effect which confers on it an anti-inflammatory action making it capable of inhibiting the disease process in the asthmatic condition especially at doses lower than it is conventionally used in the treatment of asthma.

This according to the present invention we provide the use of a compound chosen from theophylline, theobromine, pharmacologically active derivatives thereof and the pharmaceutically acceptable salts thereof in the manufacture of a pharmaceutical preparation for the chronic, prophylactic, anti-inflammatory treatment of mild asthma.

Amongst the derivatives of theophyline and theobromine, and the salts suitable for use in the present invention are Acepifylline, Bamifylline, Bufylline, Cafaminol, Caffeine, Cafedrine, Cholinetheophyllinate, Diprophylline, Enprophylline, Etophylline, Heptaminolacephyllinate, Proxyphylline, Pyridofylline, Suxamidofylline, Aminophylline, Aminophyllinehydrate and Protheobromine. Preferably theophylline or a pharmaceutically acceptable salt thereof is used.

More specifically, as demonstrated in the clinical study described in detail below it has been found that the administration of theophylline on a chronic basis at surprisingly low doses has at least three distinct bit inter-related effects on the disease process. These new actions are in addition to and distinct from the bronchodilatory properties which have been known and extensively documented.

Firstly, theophylline has a specific effect on the trafficking of circulating pro-inflammatory lymphocyte and other inflammatory cell populations from the peripheral blood to the lung. In the untreated asthmatic patient during exacerbations of the asthmatic condition, lymphocytes and other inflammatory cells are activated and recruited from the peripheral blood to the lung and are responsible for the initiation of the inflammatory changes and associated tissue damage. It has been found that the administration of theophylline on a chronic basis reduces the recruitment of these pro-inflammatory cells to the lung consequently reducing the inflammatory changes in the lung. This is associated with an improvement in the clinical symptoms of the patients and reduces the risk of long term damage to the delicate bronchial epithelium. Theophylline may also modulate the transmission of cytokines and memory T lymphocytes from the lung to the peripheral circulation and so effect a down-regulation of subsequent response.

Secondly, theophylline appears to effect a striking change in the profile of the lymphocyte subsets. T lymphocytes are divided into at least two subsets dependent on their propensity to initiate an allergic type asthmatic response ($TH_2$) or a delayed type asthmatic response ($TH_1$). Allergic asthmatic patients have a preponderance of $TH_2$ lymphocytes which initiate and fuel the chronic allergic type of asthmatic response. Theophylline has now been found to reduce the expression of the $TH_2$ type lymphocytes in such patients which consequently reduces the pulmonary inflammatory changes and improves the clinical symptoms experienced by the patients.

Thirdly, theophylline reduces the levels of cells involved in processing and presentation of the antigens such as the antigen presenting cells and tissue macrophages. This effect consequently reduces the antigen load presented to the T lymphocyte cell population and thus reduces their activation to pro-inflammatory cells.

In the light of these findings, theophylline and the other compounds mentioned above thus have an important novel clinical role in the management of asthma, that of modifying the disease process, which effects a beneficial effect on the patients clinical well being and long term condition. In addition, for those compounds which have previously been indicated for the treatment of asthma, this novel action is manifested at much lower dosages than was previously used in the management of asthma, which has the benefit of reducing the incidence and severity of side effects experienced at higher plasma levels. In the case of theophylline plasma concentrations of 1 to 9 mg/l (preferably 2.5–7.5 mg/l) which approximates to dosages of 100–400 mg daily provide adequate levels to demonstrate these beneficial effects. Ideally the above mentioned plasma levels represent mean, steady state blood plasma levels.

By mild asthma is meant for instance an asthmatic condition manifested by infrequent wheezing which is susceptible to treatment by the infrequent use of $\beta_2$-agonist (2 doses only daily) or a condition when a patient requires more than 2 doses of a $\beta_2$-agonist daily to control the wheezing for which a low dose of inhaled corticosteroids such as 400 µg beclomethasone would be indicated, and especially an asthmatic condition for which treatment in accordance with Adult Step 1 or Adult Step 2 as defined in the British Thoracic Society Guidelines on the Management of Asthma, Thorax 1993: 48, (Suppl.); S1–S24 is prescribed.

Hitherto theophylline has not been widely used for paediatric use as, at the previously used doses, it has been perceived as having an undesirable side effect profile. The present new and unexpected finding, that the above mentioned compounds, especially theophylline and salts thereof, are effective at lower doses means that this beneficial prophylactic treatment should prove to be more widely accepted for paediatric use.

In accordance with the present invention theophylline or a pharmaceutically acceptable salt thereof or one of the other compounds mentioned above may be used as a partial or complete replacement for or as an add-on therapy to treatment with $\beta_2$ mimetics such as salbutamol, in view of their anti-inflammatory activity. At the dosage levels recommended as preferred herein any bronchodilatory effect will be extremely mild or not present but would, if present, nonetheless, supplement that of the $\beta_2$ mimetic. The treatment would also be indicated as an add-on or replacement therapy to standard low dose steroidal treatment for asthma where the anti-inflammatory effect would supplement that of the steroid (if used) and possibly enable the reduction or even elimination of the steroidal dose, whilst any mild bronchodilatory effect would also be beneficial.

The pharmaceutical preparation may be one which van be given orally, intravenously, inhalation per nasally, per rectum or transdermally.

Preferred compositions for use according to the invention may suitably take the form of tablets, capsules, granules, shperoids, powders or liquid preparations.

Tablets and capsules for oral administration may be prepared by conventional techniques with pharmaceutically acceptable excipients such as binding agents, fillers, lubricants, disintegrants, wetting agents, colourants and flavours. The tablets may be coated according to methods well known in the art.

Preferably the compositions produces or used in accordance with the invention is in dosage unit form, e.g. in tablet or filled capsule form. Further, it is preferred that the active substance be in controlled release form. In this latter case, compositions prepared in accordance with the invention will typically contain 100 to 200 mg of theophylline or an equivalent amount of other active substance.

Suitable materials for inclusion in a controlled release matrix include, for example:
- (a) Hydrophilic or hydrophobic polymers, such as gums, cellulose esters, cellulose ethers, protein derived materials, nylon, acrylic resins, polyactic acid, polyvinylchloride, starches, polyvinylpyrrolidones, cellulose acetate phthalate. Of these polymers, cellulose ethers especially substituted cellulose ethers such as alkylcelluloses (such as ethylcellulose), $C_{1-6}$ hydroalkylcelluloses (such as hydroxypropylcellulose and especially hydroxyethyl cellulose) and acrylic resins (for example methacrylates such as methacrylic acid copolymers) are preferred. The controlled release matrix may conveniently contain between 1% and 80% (by weight) of the hydrophilic or hydrophobic polymer.
- (b) Digestible, long chain ($C_8$–$C_{50}$, especially $C_8$–$C_{40}$), substituted or unsubstituted hydrocarbons, such as fatty acids, hydrogenated vegetable oils, such as Cutina (Trade Mark), fatty alcohols (such as lauryl, myristyl, stearyl, cetyl or preferably cetostearyl alcohol), glyceryl esters of fatty acids for example glyceryl monostearate mineral oils and waxes (such as beeswax, glycowax, caster wax or carnauba wax). Hydrocarbons having a melting point of between 20° C. and 90° C. are preferred. Of these long chain hydrocarbon materials, fatty (aliphatic) alcohols are preferred. The matrix may contain up to 60% (by weight) of at least one digestible, long chain hydrocarbon.
- (c) Polyalkylene glycols. The matrix may contain up to 60% (by weight) of at least one polyalkylene glycol.

A suitable matrix comprises one or more $C_{12}$–$C_{36}$, preferably $C_{14}$–$C_{22}$ aliphatic alcohols and/or one or more hydrogenated vegetable oils.

A particularly suitable matrix comprises one or more alkylcelluloses, one or more $C^{12-36}$, (preferably $C_{14}$–$C_{22}$) aliphatic alcohols and optionally one or more polyalkylene glycols.

Preferably the matrix contains between 0.5% and 60%, especially between 1% and 50% (by weight) of the cellulose ether.

The acrylic resin is preferably a methacylate such as methacrylic acid copolymer USNF Type A (Eudragit L, Trade Mark), Type B (Eudragit S, Trade Mark), Type C (Eudragit L 100-55, Trade Mark), Eudragit NE 30D, Eudragit E, Eudragit RL and Eudragit RS. Preferably the matrix contains between 0.5% and 60% by weight, particularly between 1% and 50% by weight of the acrylic resin.

In the absence of polyalkylene glycol, the matrix preferably contains between 1% and 40%, especially between 2% and 36% (by weight) of the aliphatic alcohol. When polyalkylene glycol is present in the oral dosage form, then the combined weight of the aliphatic alcohol and the polyalkylene glycol preferably constitutes between 2% and 40%, especially between 2% and 36% (by weight) of the matrix.

The polyalkylene glycol may be, for example, polypropylene glycol or, which is preferred, polyethylene glycol. The number average molecular weight of the at least one polyalkylene glycol is preferably between 200 and 15000 especially between 400 and 12000.

The medicament-containing controlled release matrix can readily be prepared by dispersing the active ingredient in the controlled release system using conventional pharmaceutical techniques such as wet granulation, dry blending, dry granulation or coprecipitation.

The efficacy of theophylline in controlling the T-lymphocyte population of lung tissue in asthmatic conditions is evidenced by the following clinical trials.

PATIENTS

Asthmatic patients aged 25 to 70 years, of whom eighteen were female, were studied. All had continuously used oral theophylline/aminophylline over the last 6 months. Seventeen patients had at least one positive reaction to skin prick testing with common aeroallergent (allergic); the remaining ten patients had negative responses (non-allergic). All patients were taking inhaled short-acting $\beta_2$-agonists as required for symptom control and all were taking inhaled steroids (mean dose 1548 µg/day of beclomethasone dipropionate or budesonide) at a dose that had not changed within 8 weeks of the study. All patients had been taking a slow-release oral theophylline preparation for at least 6 months (Phyllocontin: mean dose 562 mg daily in 16 patients; Uniphylline: mean dose 573 mg in 11 patients). Three patients were taking maintenance oral steroids (5, 7.5 and 10 mg prednisolone daily) at a dose that had not changed for 8 weeks prior to the study. None of the patients had a lower respiratory tract infection or an exacerbation of asthma within 8 weeks of commenting the study. All patients had a forced expiratory volume in one second ($FEV_1$) of >1.0 L with a range from 32–117% predicted (mean 70.5%), and all patients had a >15% variability in peak expiratory flow (PEF).

In order to compare the lympocyte subpopulations with patients not taking theophylline, venous blood was obtained from 8 asthmatic patients (21–69, means 37.6 yr) who were also receiving inhaled steroids (mean daily dose 1028 µg), but whom had never received theophylline.

CLINICAL MEASUREMENTS $FEV_1$ and vital capacity (VC) were measured at each clinic visit as the highest of three recording using a dry spirometer (Vitallograph, Cambridge, UK).

PERIPHERAL BLOOD MEASUREMENTS

Venous blood (10 ml) was taken at each clinic visit and collected into a citrated tube. An aliquot was taken for full blood count using an automated blood count analyzer (Coulter Electronics, Hialeah, FL). Slides were prepared for measurement of differential leukocyte count and eosinophil numbers using May-Grunewald-Giemsa stain.

Populations of leukocytes were identified by dual colour cytometry using directly conjugated monoclonal antibodies (MoAbs; Becton Dickinson, Mountain View, CA). An aliquot of whole blood (50 $\mu$l) was incubated with 20 $\mu$l fluorochrome-labelled MoAb for 15 minutes in the dark at 4° C. MoAbs were labelled with either fluorescein isothiocyanate (FITC) or phycoerthrin (PE). Differentially labelled pairs included antibodies against CD45 and CD14 (FITC/PE respectively) for leukocytes and monocytes; CD3/CD19 (FITC/PE) for T- and B-lymphocytes; CD4/CD8 (FITC/PE) for helper and suppressor T-cells. In addition CD4 and CD8 cells were also labelled with FITC MoAb and dual stained with PE-labelled MoAbs against HLA-DR and interleukin-2 receptor (CD25). Eosinophils were stained with EG2 antibody (Pharmacia, Uppsala, Sweden) which detects the cleaved form of eosinophil cationic protein and therefore activated cells. Red cells were lysed with 2 ml hypo-osmolar solution (FACS Brand Lysing Solution, Becton Dickinson) and the suspension spun at 400×g for 5 minutes. The supernatant was aspirated and the pellet washed in 2 ml phosphate buffered saline containing 0.01% sodium azide and resuspended in 0.5% paraformaldehyde fixative. Cytofluorimetric analysis was performed on a FACScan flow cytometer (Becton Dickinson) with scatter gates on the lymphocyte fraction using excitation 488 nm. The number of immonofluorescent positive cells was determined from 10,000 analyzed cells and results expressed as % positive lymphocytes and absolute numbers of cells/mm$^3$.

PLASMA THEOPHYLLINE

Theophylline concentrations were measured in stored plasma samples taken at each clinic visit using high pressure liquid chromatography with ultraviolet detection. Quantification was by reference to a standardized calibration curve which was linear over the range 0–25 mg/L. The mean steady state plasma concentration was computed by Bayesian analysis.

PROTOCOL

At the first visit clinical details were recorded, spirometry and PEF recorded and a blood sample taken. For the first two weeks patients continued to take their currently prescribed anti-asthma treatment and recorded symptoms, inhaled $\beta_2$-agonist usage and PEF twice daily at home on a diary card. After two weeks patients attended the clinic and were randomized in a double-blind manner to receive either the same dose of Phyllocontin/Uniphyllin or an identical placebo in a dose which they had previously been taken. Patients completed the study after two weeks when they attended the clinic again. At each clinic visit blood was taken for leukocyte measurements and plasma theophylline, and spirometry and PEF were recorded.

BRONCHIAL BIOPSY

Eight patients (25–61, mean 47 years, 7 female) were selected randomly in a blinded fashion from those who has successfully completed the first part of the study. Bronchial biopsy was undertaken by the same operator following treatment with theophylline and again two weeks after substitution of theophylline by placebo. Fiberoptic bronchoscopy was performed using a fiberoptic bronchoscope (Olympus, Tokyo), after premedication with albuterol (2.5 mg via nebulizer), atropine (0.6 mg i.v.) midazolam (mean dose 5–10 mg i.v.) for sedation and 2% lidocaine for local anesthesia of the upper respiratory tract. Bronchial biopsies were taken using alligator forceps from three or four sites in segmental or subsegmental bronchi for alternate lower lobes. Nebulized albuterol was administered after the procedure. All patients tolerated the procedure well and there was no instances of bronchoconstriction.

EXAMINATION OF BIOPSY SPECIMENS

Biopsy specimens were mounted in Tissue-Tek, snap-frozen in sopentane over liquid nitrogen and stored in liquid nitrogen until required. Cryostat sections (6 $\mu$m) were air dried, fixed in acetone and stored at −70° C. for later analysis. Some sections were stained with hematoxylin and eosin for histological studies. Sections were stained with mouse MoAbs against cd45, CD3, CD4, CD8, CD14, CD25 (Becton Dickinson) and EG2 (Pharmacia). The primary MoAb was followed by mouse monoclonal anti-alkaline phosphatase and alkaline phosphatase complexes (APAAP). Sites of alkaline phophatase fixation were identified by incubation with substrate (4 mM fast red TR salt dissolved in 100 mM Tris buffer, pH 8.2, containing naphthol as MX phosphate and 0.5 mM levamisole to inhibit non-specific staining), which was prepared and filtered immediately prior to use. Sections were counterstained with Harris' hematoxylin. When the primary MoAb was omitted there was an absence of staining. Sections were examined "blind" microscopically using a ×40 objective and the number of positively stained cells per 0.25 mm length of basement membrane was ascertained both under (depth=0.05 mm) the basement membrane and within the epithelium. At least four (=1 mm) and usually 5–10 lengths were examined per specimen. Average values are presented.

RESULTS

Clinical Measurements

Twenty-five patients completed the study; two patients were withdrawn from the study, one of whom developed an acute exacerbation of asthma within 24 hours of theophylline withdrawal during which the PEF fell to 120 L/min, requiring nebulized albuterol, a course of oral steroids and restitution of theophylline. The second patient developed an exacerbation following an upper respiratory tract infection during theophyline treatment and required a course of oral steroids.

There was a significant reduction in $FEV_1$ and PEF at the end of the placebo period compared to the end of the theophylline period. The differences between treatment periods were more pronounced in patients with plasma theophylline values >5 mg/L (n=20), and there was no significant difference in patients with plasma theophylline values of <5 mg/L (n=5).

Effect on Blood Cells

There was no difference in total leukocyte counts or lymphocyte counts between theophylline and placebo treatment periods (Table 1). There was a significant decrease in monocyte (CD14$^+$) count when on placebo (7.1±0.43% on placebo compared to 7.8±0.60% on theophylline, p<0.05) and this was more marked in patients with theophylline levels of >5 mg/L (7.0±0.52% on placebo versus 8.0±0.73%). There was no change in total eosinophil count or in EG2$^+$ cells between the two periods, although there was a trend towards more eosinophils following theophylline withdrawal.

Flow cytometric analysis showed no significant difference in either absolute number or percentage total T-cells (CD3$^+$) between the two treatment periods. When activated T-cells were measured as either HLA-DR$^+$ (CD3$^+$/DR$^+$) or T-cells expressing the interleukin-2 receptor (CD3$^+$/CD25$^+$), there were fewer activated cells during the placebo period, although the differences were not significant. In contrast when activated CD4$^+$ and CD8$^+$ populations were measured significant changes were observed with theophylline withdrawal, with a significant reduction in CD8$^+$/DR$^+$ cells (p<0.05), which was not observed in the patients with theophylline values of <5 mg/L. The asthmatic patients who had never been treated with theophylline had values of CD8$^+$DR$^+$ cells similar to the values found after placebo. There was also a reduction in CD4$^+$/CD25$^+$ cells after theophylline withdrawal, but this was seen only in patients with theophylline values of <5 mg/L (p<0.01). The proportion of CD4$^+$/CD25$^+$ cells in theophylline naive patients was not significantly different from values during the placebo period, but significantly less than the proportion during treatment with theophylline in patients who achieved plasma values of <5 mg/L (p<0.05). Similarly the proportion of activated T-cells (CD3$^+$/CD25$^+$) was significantly less in naive control asthmatic subjects than in patients receiving theophylline (Table 1).

When lympocyte populations were analyzed separately for allergic and non-allergic asthmatic patients, there was no difference in CD4$^+$ population during either treatment period, but there was a greater decrease in CD8$^+$/DR$_+$ cells during theophylline withdrawal in the non-allergic patients (12.1±1.45% during theophylline treatment compared to 8.3±0.42% during placebo, p<0.01).

Biopsy Study

The effects of theophylline compared to placebo treatment on spirometry and symptom scores in the 8 patients who went on to the biopsy study were very similar to the results obtained for the whole group.

Plasma theophylline concentrations were 7.7±0.81 mg/L during theophylline treatment and undetectable during placebo treatment.

The cell counts in the bronchial biopsies showed significant differences between the theophylline and placebo (Table 2). There was a significant increase in CD8$^+$ cells in the mucosa during theophylline withdrawal (p<0.05). There was also an increase in CD3$^+$, CD4$^+$, CD25$^+$ and CD14$^+$ cells during theophylline withdrawal, although these changes did not achieve statistical significance. There was also an increase in EG2$^+$ cells on theophylline withdrawal. A significant increase in CD4$^+$ cells was found within the airway epithelium (1.5±0.49/100 epithelial cells on theophylline vs 4.3±0.98 on placebo, p<0.05).

There was a significant inverse correlation between the number of CD3$^+$ and CD4$^+$ cells (r=0.74, p<0.05) in peripheral blood and biopsies.

TABLE 1

Effect of theophylline withdrawal on circulating leukocytes

| Leukocytes | Theophylline | Placebo | Naive Controls |
|---|---|---|---|
| WBC (× 10$^9$/L) | 8.0 ± 0.5 | 7.8 ± 0.4 | 8.8 ± 1.9 |
| Lymphocytes | 22.0 ± 1.5 | 22.4 ± 1.3 | 29.0 ± 4.0 |
| CD3$^+$ (% lymphos) | 72.5 ± 1.6 | 73.8 ± 1.2 | 69.0 ± 2.5 |
| CD3$^+$CD25$^+$ (% lymphos) | 22.9 ± 1.7 | 22.2 ± 1.5 | 12.8 ± 2.3$^{++}$ |
| CD3/DR$^+$ (% lymphos) | 17.4 ± 2.0 | 16.5 ± 1.3 | 13.7 ± 2.6 |
| CD4$^+$ (% lymphos) | 40.3 ± 2.1 | 41.2 ± 1.7 | 42.0 ± 3.3 |
| CD4$^+$/CD25$^+$ (% lymphos) | 18.3 ± 1.5 | 16.5 ± 1.3 | 12.0 ± 2.3$^+$ |
| CD4/DR$^+$ (% lymphos) | 6.6 ± 0.8 | 6.5 ± 0.7 | 4.9 ± 1.0 |
| CD8$^+$ (% lymphos) | 35.3 ± 2.4 | 33.8 ± 1.9 | 32.3 ± 3.7 |
| CD8$^+$/CD25$^+$ (% lymphos) | 3.8 ± 0.6 | 4.1 ± 0.7 | 1.1 ± 0.3$^{++}$ |
| CD8/DR$^+$ (% lymphos) | 12.1 ± 2.0 | 10.1 ± 1.5* | 8.5 ± 2.0 |
| CD18$^+$ (% lymphos) | 9.6 ± 1.1 | 10.3 ± 1.2 | 14.1 ± 2.4 |
| Monocytes (CD14$^+$, % WBC) | 7.8 ± 0.6 | 7.1 ± 0.4* | 8.9 ± 1.2 |
| Eosinophils (% WBC) | 4.8 ± 0.7 | 5.1 ± 0.7 | 5.5 ± 1.1 |
| EG2$^+$ (% eos) | 50.5 ± 4.7 | 56.0 ± 4.8 | 35.7 ± 10.8 |

WBC = total leukocyte count. Mean values ± SEM are shown.
Difference between theophylline and placebo periods: *P = 0.05
Difference between naive controls and theophylline treatment period $^+$P = 0.005, $^{++}$P = 0.01

We claim:

1. A method for the chronic, prophylactic anti-inflammatory treatment of asthma comprising administering a pharmaceutical preparation containing an amount of theophylline or pharmacologically acceptable salts thereof, to provide a mean steady state plasma level of 1 to less than 5 mg/L.

2. The method according to claim 1 wherein said theophylline or pharmaceutically acceptable salt thereof is prepared in a dosage form for dosing at 50 to 600 mg per day in single or divided doses.

3. The method according to claim 1, wherein the pharmaceutical preparation is for use as an add-on therapy or to replace completely or partially treatment with corticosteroids.

4. The method according to claim 1, wherein the pharmaceutical preparation is for use as an add-on or replacement therapy for treatment with a β$_2$-mimetic.

5. The method according to claim 1, wherein the amount of theophylline or pharmaceutically acceptable salt thereof provides a mean, steady state blood plasma level of 2.5 to less than 5 mg/L.

6. A method of treating asthma comprising administering a pharmaceutical preparation containing theophylline or pharmacologically acceptable salts thereof, to provide a mean steady state plasma level of 1 to less than 5 mg/L, wherein substantially no, or only a mild, bronchodilatory effect is exhibited.

* * * * *